United States Patent [19]

Lo et al.

[11] Patent Number: 4,627,014

[45] Date of Patent: Dec. 2, 1986

[54] METHOD AND APPARATUS FOR DETERMINATION OF AN ANALYTE AND METHOD OF CALIBRATING SUCH APPARATUS

[75] Inventors: Donald H. Lo; Tai-Wing Wu; Mark W. Bailey, all of Rochester, N.Y.

[73] Assignee: Eastman Kodak Company, Rochester, N.Y.

[21] Appl. No.: 597,878

[22] Filed: Apr. 9, 1984

[51] Int. Cl.[4] .................... G01J 3/28; G01N 15/06; G01F 25/00
[52] U.S. Cl. ...................... 364/571; 364/497; 422/67; 436/97; 356/300; 356/39
[58] Field of Search .............. 364/571, 497; 356/311, 356/51, 300, 326, 328, 39, 40; 422/66, 67; 436/46, 97; 250/440.1

[56] References Cited

U.S. PATENT DOCUMENTS

| | | | |
|---|---|---|---|
| 3,914,054 | 10/1975 | Hadeishi | 356/311 X |
| 3,960,497 | 6/1976 | Acord | 422/67 |
| 4,043,756 | 8/1977 | Sommervold | 422/67 X |
| 4,061,469 | 12/1977 | DuBose | 422/67 X |
| 4,069,017 | 1/1978 | Wu et al. | 23/230 B |
| 4,202,033 | 5/1980 | Strobel | 364/571 X |
| 4,218,746 | 8/1980 | Koshiishi | 364/497 X |
| 4,298,571 | 11/1981 | DiFulvio et al. | 422/64 X |
| 4,303,337 | 12/1981 | James et al. | 356/40 X |
| 4,338,095 | 7/1982 | Wu | 422/56 |
| 4,412,005 | 10/1983 | Wu | 436/97 |
| 4,420,566 | 12/1983 | Jessop et al. | 436/46 |
| 4,436,812 | 3/1984 | Endoh et al. | 364/497 X |
| 4,457,808 | 7/1984 | Taylor et al. | 364/571 X |
| 4,468,467 | 8/1984 | Babb et al. | 436/97 |
| 4,468,742 | 8/1984 | Jenden et al. | 364/571 X |

OTHER PUBLICATIONS

Pliskin, W. A., "Calibration of Spectrophotometers", IBM Technical Disclosure Bulletin, vol. 12, No. 1, Jun. 1969, p. 191.
Hahn et al., Clin. Chem., 25(6), pp. 951–959 (1979).
Dappen et al., Clin. Chem., 29(1), pp. 37–41 (1983).

Primary Examiner—Errol A. Krass
Assistant Examiner—Joseph L. Dixon
Attorney, Agent, or Firm—J. Lanny Tucker

[57] ABSTRACT

A method and apparatus are described for the determination of an analyte in an aqueous liquid while eliminating the biasing effect of unknown interferents which are preformed or formed in situ during the determination. The method comprises physically contacting a sample of the liquid with an interactive composition for the analyte; measuring the spectrophotometric responses generated by such contact at a primary wavelength $\lambda_1$ and one or more secondary wavelengths $\lambda_2, \lambda_3, \ldots \lambda_n$; and determining analyte concentration or activity using the equation:

$$C = a_0 + a_1[A_1 + \alpha_1 A_2 + \ldots + \alpha_{n-1} A_n]$$

wherein C is analyte concentration or activity, $A_1, A_2, \ldots A_n$ are the spectrophotometric responses observed at $\lambda_1, \lambda_2, \ldots \lambda_n$, respectively; and $a_0, a_1$, and $\alpha_1, \alpha_2, \ldots \alpha_{n-1}$ are constants determined according to a calibrating method, also described herein. Such calibrating method is an empirical means for determining and recording in a chemical analyzer the $a_0, a_1$, and $\alpha_1, \alpha_2, \ldots \alpha_{n-1}$ constants essential for making the analyte determination.

18 Claims, 4 Drawing Figures

METHOD AND APPARATUS FOR DETERMINATION OF AN ANALYTE AND METHOD OF CALIBRATING SUCH APPARATUS

FIELD OF THE INVENTION

The present invention relates to a method and apparatus for determining an analyte in an aqueous liquid, such as a biological fluid. In particular it relates to a clinical chemistry analyzer and method of using same to determine analytes, such as bilirubin, in human sera. This invention also relates to a method for calibrating an apparatus, such as a chemical analyzer, to provide a means for making analyte determinations which are not biased by undefined interferents.

BACKGROUND OF THE INVENTION

In order to provide desired preventative or diagnostic health care, a physician must often determine the level of various analytes in a patient's blood, urine or other body fluids. For example, the level of glucose is often important in the diagnosis and subsequent treatment of diabetes. The level of hemoglobin in the blood is often important for effective diagnosis and treatment of anemia or other related blood abnormalities.

Another important analyte which physicians often monitor is bilirubin. Bilirubin is a degradation product of hemoglobin. Approximately 200 to 230 mg of bilirubin and its derivatives are formed each day in the normal human adult. As part of normal human metabolic processes, the major portion of this daily bilirubin production is excreted or degraded into other derivatives.

Excessive amounts of bilirubin occur within the human body through overproduction of bilirubin as in the case of excessive hemolysis or by retention of bilirubin due, for example, to liver failure. The result of excessive bilirubin within the human body is jaundice. Jaundice is characterized by markedly elevated serum bilirubin levels, for example, 10 mg of bilirubin per dL of serum or higher compared with the normal adult range of 0.1 to about 1 mg of bilirubin per dL of serum. There is increasing evidence that excessive amounts of bilirubin in the blood lead to an undesirable increase in bilirubin concentration within body cells which interferes with various cellular processes. Given this background, the clinical diagnostic significance of bilirubin, in tests for liver and other related organ functions, is self evident.

Perhaps the most widely used assay for bilirubin has been the so called diazo method. In this method, a sample of liquid suspected of containing bilirubin is contacted with a reagent composition which includes a diazonium salt. The diazonium salt reacts with bilirubin to form two azobilirubin fragments. The azobilirubin has an extinction coefficient which is higher than that of bilirubin itself and is easily detectable.

Many diazonium salts have been suggested for use in the diazo method for determining bilirubin. For example, certain 2,4- and 2,5-phenyldiazonium salts (e.g. 2,4- and 2,5-dichlorophenyldiazonium salts) and diazotized sulfanilamide have been used for the detection of bilirubin in serum and urine. However, methods using these diazonium salts are known to be relatively insensitive. Further, some of these diazonium salts, when dry, are explosively unstable, i.e. subject to shock induced decomposition. Thus, handling of these compounds in bilirubin assays, and particularly dry assays, is quite hazardous.

Certain substituted sulfanilamide and carbonamide diazonium salts which are less prone to shock induced decomposition have been found useful in bilirubin assays. These salts and assays are the subject of U.S. Pat. No. 4,468,467 (issued Aug. 28, 1984 to Babb et al). Those salts and assays represent a significant improvement in the clinical chemistry art, overcoming the shortcomings of previously-known bilirubin assays. This improved assay is also described by Babb and co-authors in Clin. Chem., 29(1), pp. 37–41 (1983).

Many substances, both foreign and native, are present in biological fluids, which substances cause serious interferences in the quantitative analyses of analytes, including bilirubin. Notwithstanding the significant improvement provided by the invention of Babb and Dappen noted hereinabove, there was a need prior to the instant invention to provide further improvements in the bilirubin assay. For example, with a small percentage of patient serum samples, e.g. those obtained from hemodialysis or other renal-defective patients, interferences were observed to be influential in the end result, detracting from assay accuracy. It is desirable to remove such interferences, thereby providing an assay that is highly accurate with all patient samples including samples obtained from patients having kidney problems.

Known procedures for eliminating interferences in assays include sample pretreatment, sample blanking and polychromatic (i.e. multiple wavelength) analyses. Each of these procedures, however, has its disadvantages. Sample pretreatment is a tedious and imprecise operation and is not readily adaptable to dry chemistry assays. Sample blanking doubles the effort, reagent amount and cost of each assay while being ineffective with regard to interferents formed in situ during the assay. The known polychromatic analysis requires pure standards and knowledge of the exact molecular identity or concentrations of predetermined interferents. See, e.g. Hahn et al, Clin. Chem., 25(6), pp. 951–959 (1979). Again, this technique would not be useful where the interferent is unknown and cannot be determined prior to the assay.

None of these known procedures has proved effective for eliminating the observed interference in the bilirubin assay described and claimed in U.S. Pat. No. 4,468,467 noted hereinabove. Neither the identity of the interferent nor its concentration (which can vary from sample to sample) is known. It is likely that the interferent is formed during the assay. This precludes use of known techniques for removing the effects of interferents.

Therefore, there is a need in the art for a means for overcoming the effect of undefined interferents, such as those formed in situ, i.e. during the analysis. In particular, there is a need for a means whereby assay accuracy for all patient samples, not just some samples, is achieved.

SUMMARY OF THE INVENTION

The present invention provides a means for overcoming the effect of undefined interferents in the determination of an analyte, such as total bilirubin. This invention is practiced with an empirical calibration procedure whereby a chemical analyzer is adapted to automatically correct the assay results for any bias caused by the undefined interferent. Once the analyzer is calibrated, the assay of this invention can be performed to obtain accurate results for a population of test samples some of which may contain or be disposed to form an interferent and some of which may not. This advantage is particularly expedient when the unknown interferent is formed in situ, i.e. during the assay, and hence cannot be predetermined.

The present invention is particularly useful for providing a means whereby accurate total bilirubin assays can be made with an unrestricted population of serum samples. Hence, it is inconsequential to the accuracy of the assay if some of the serum samples are obtained from patients who are undergoing hemodialysis or have severe renal disorders which may otherwise produce incorrect results. Such serum samples are known as uremic serum samples.

Therefore, this invention provides a method for calibrating a chemical analyzer useful in the determination of an analyte in an aqueous liquid. Such an analyzer comprises (a) spectrophotometric means for detecting "n" spectrophotometric responses $A_1, A_2, \ldots A_n$ resulting when a sample of the liquid is contacted with an interactive composition for the analyte, and (b) means for calculating the concentration or activity C of the analyte in said sample using the equation (I):

$$C = a_0 + a_1[A_1 + \alpha_1 A_2 + \ldots + \alpha_{n-1} A_n]$$

wherein $a_0, a_1, \alpha_1, \alpha_2, \ldots \alpha_{n-1}$ are defined hereinafter. This calibrating method comprises the steps of:

A. from a multiplicity of patient test samples of unknown analyte concentration or activity, identifying first and second patient test samples having substantially the same analyte concentration or activity, the first sample exhibiting a significant bias in analyte concentration or activity and the second sample exhibiting no significant bias in analyte concentration or activity measured at a primary wavelength $\lambda_1$;

B. making a spectral absorption scan of each of the samples identified in step A;

C. identifying absorption bands from the spectral scans where differences in absorbance between said scans can be observed, and selecting at least one secondary wavelength from the group of secondary wavelengths $\lambda_2, \lambda_3, \ldots \lambda_n$ representative of the absorption bands of both said first and second patient samples, respectively, wherein n represents the number of absorption bands;

D. using a multiplicity of patient test samples of known analyte concentration or activity, determining a linear regression line and its intercept and slopes using the equation (II):

$$C = a_0 + a_1 A_1 + a_2 A_2 + \ldots + a_n A_n$$

wherein C is analyte concentration or activity; $a_0$ is the intercept of the line; $A_1, A_2, \ldots A_n$ are the spectrophotometric responses measured at $\lambda_1, \lambda_2, \ldots \lambda_n$ respectively; and $a_1, a_2, \ldots a_n$ are the slopes of the line relating the spectrophotometric responses at $\lambda_1, \lambda_2, \ldots \lambda_n$, respectively, to the analyte concentration or activity;

E. using the results of step D to determine constants $\alpha_1, \alpha_2, \ldots \alpha_{n-1}$ for equation (I) above using the equation (III):

$$\alpha_i = (a_{i+1})/a_1$$

wherein
i = 1 to (n−1); and

F. recording in the analyzer the values of constants $a_0, a_1,$ and $\alpha_1, \alpha_2, \ldots \alpha_{n-1}$ for use in equation I above.

This invention also provides a method for the determination of an analyte in an aqueous liquid. Such method comprises the steps of:

(A) physically contacting a sample of the liquid with an interactive composition for the analyte;

(B) measuring the spectrophotometric responses $A_1, A_2, \ldots A_n$ resulting from such contact at, respectively, a primary wavelength $\lambda_1$ and at n secondary wavelengths selected from secondary wavelengths $\lambda_2, \lambda_3, \ldots \lambda_n$ determined according to the calibration method described hereinabove; and (C) determining the concentration or activity C of the analyte using the equation (I):

$$C = a_0 + a_1[A_1 + \alpha_1 A_2 + \ldots + \alpha_{n-1} A_n]$$

wherein the constants $a_0, a_1$ and $\alpha_1, \alpha_2, \ldots \alpha_{n-1}$ are determined according to the calibration method described hereinabove, for as many n secondary wavelengths as are used in step (B).

Further, this invention provides a chemical analyzer for the determination of an analyte in an aqueous liquid in contact with an interactive composition for the analyte. This novel analyzer comprises:

means for measuring the spectrophotometric responses $A_1, A_2, \ldots A_n$ at, respectively, a primary wavelength $\lambda_1$ and at n secondary wavelengths selected from the secondary wavelengths $\lambda_2, \lambda_3, \ldots \lambda_n$; and means for determining the concentration or activity C of the analyte using the equation (I):

$$C = a_0 + a_1[A_1 + \alpha_1 A_2 + \ldots + \alpha_{n-1} A_n]$$

wherein the constants $a_0, a_1$ and $\alpha_1, \alpha_2, \ldots \alpha_{n-1}$ are determined according to the calibration method described hereinabove, for as many n secondary wavelengths as are used.

DETAILED DESCRIPTION OF THE INVENTION

Figure 1:
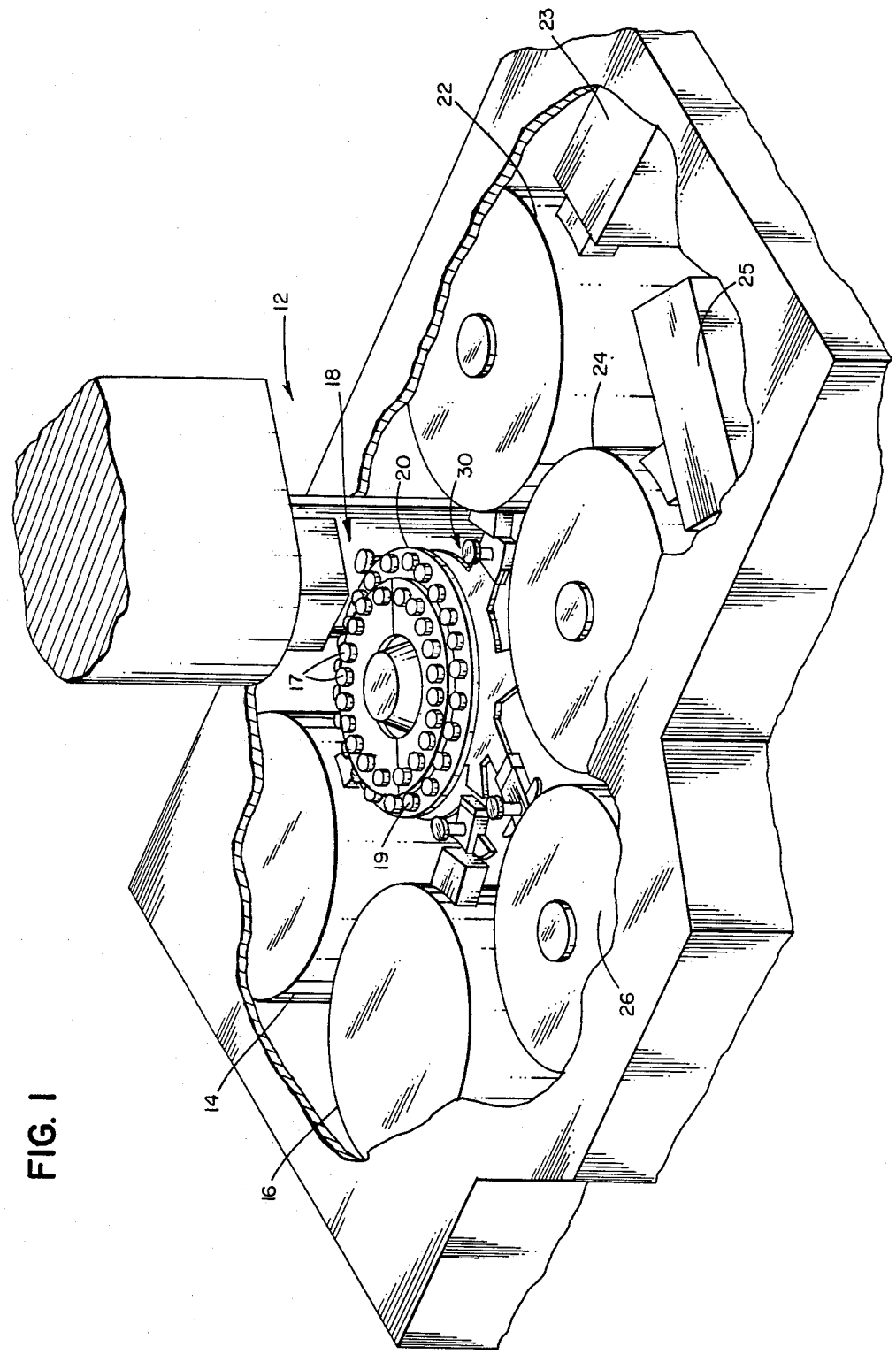
FIG. 1 is a partial perspective view of a chemical analyzer according to the present invention.

The present invention is useful for measuring an analyte, such as total bilirubin, hemoglobin, glucose, uric acid, metal ions and other substances in an aqueous liquid, such as a biological liquid obtained from an animal or human. For example, the analyte can be determined in diluted or undiluted serum, plasma, whole blood, urine, cerebral spinal fluid and other body fluids with this method. It is particularly advantageous to determine total bilirubin in uremic serum with this invention.

An analyte is determined by the present invention by first physically contacting a specimen sample suspected of containing the analyte with an interactive composition for that analyte. In other words, the analyte is subjected to a composition which interacts with it in such a manner as to provide a detectable spectrophotometric response of some kind, e.g. an increase or decrease in a detectable dye which can be detected by a suitable spectrophotometric detector, or to provide a product which of itself is not detectable, but which can further react to provide a detectable response. A detectable dye can be provided either by interaction with a dye-providing material, or by dye release from a preformed dye. The term "interaction" is meant to refer to chemical activity, catalytic activity as in the formation of an enzyme-substrate complex, immunogenic activity as in an antigen-antibody reaction, and any other form of electrical, chemical or physical interaction that can release, produce or otherwise provide a detectable response which is directly or indirectly indicative of the presence or concentration of a particular analyte. More details regarding such interactions are given, for example, in U.S. Pat. No. 3,992,158 (issued Nov. 16, 1976 to Przybylowicz et al).

In one embodiment, this invention can be used to determine hemoglobin and to avoid the potential interferences which can cause inaccurate hemoglobin determinations in, e.g. lipemic samples. In such determinations, hemoglobin is converted to a colorimetrically detectable species using a suitable interactive composition for hemoglobin, e.g. the conventional Drabkin's reagents (i.e. ferricyanate and cyanate).

In assays for specific metallic ions practiced according to this invention, the interactive composition for a specific ion can be a chelating compound or moiety which will react or complex with that metal ion to provide a colorimetrically detectable species. In some instances, these chelating materials may be interfered with by other metal ions thereby causing premature or insufficient reaction or complexation with the desired ion. This invention can be used to reduce the effect of such interferences. In other instances, the interference by a colored organic species with metal chelation can be reduced, e.g. the interference of bilirubin with iron chelation.

In a preferred embodiment, the methods and apparatus of this invention provide a highly accurate means for determining total bilirubin whereby bilirubin is detected with a reagent composition which includes a diazonium salt (or diazo reagent). This salt reacts with bilirubin to form colorimetrically detectable azobilirubin fragments as noted hereinabove in the Background of the Invention.

Any of a great number of diazo reagents can be used in this invention although some, because of their instability in dry form, may be limited in utility to solution or "wet" assay. Examples of useful diazo reagents include 2,6-dichlorobenzene diazonium salts and the like as described, for example, in U.S. Pat. No. 3,880,588 (issued Apr. 29, 1975 to Rittersdorf et al); 2,4-dichlorobenzenediazonium salt and the like as described in U.S. Pat. No. 4,038,031 (issued July 26, 1977 to Lam); diazotized sulfanilic acid; diazotized 2,4-dichloroaniline; diazonium fluoroborate; and others known in the art.

Particularly useful diazonium salts are those described in U.S. Pat. No. 4,468,467, noted hereinabove. Those salts have the advantage of being extremely resistant to shock induced decomposition and therefore, can be used for both solution and dry assays. These diazonium salts have the structure:

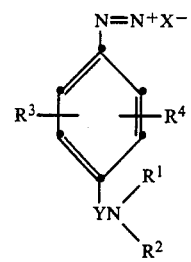

wherein $X^-$ is a stabilizing anion, Y is $-CO-$ or $-SO_2-$; $R^1$ and $R^2$ are independently selected from hydrogen, substituted or unsubstituted alkyl, preferably having from 1 to 20 carbon atoms (e.g. methyl, chloromethyl, isopropyl, dodecyl), substituted or unsubstituted alkaryl, preferably having from 7 to 20 carbon atoms in the alkaryl backbone (e.g. benzyl), substituted or unsubstituted aryl, preferably having from 6 to 14 carbon atoms in the aromatic backbone (e.g. phenyl, xylyl, p-methoxyphenyl, naphthyl), and carboxyalkyl and hydroxyalkyl, preferably wherein the alkyl group is lower alkyl, i.e. having 1 to 4 carbon atoms [e.g. carboxymethyl, carboxyethyl, hydroxymethyl, hydroxyethyl, tris(hydroxymethyl)methyl and hydroxy-4-n-butyl], and more preferably are not both hydrogen; and $R^3$ and $R^4$ are independently selected from the groups which are electron donor groups or mildly electron withdrawing groups, such that the sum of the Hammett sigma values for $R^3$ and $R^4$ does not exceed $+0.4$. Examples of such groups include hydrogen, halogen (e.g. chloro, bromo), lower alkyl preferably of 1 to 4 carbon atoms (e.g. methyl, propyl), alkylthio preferably of 1 to 4 carbon atoms (e.g. methylthio), lower alkoxy preferably of 1 to 4 carbon atoms (e.g. methoxy, ethoxy), aralkoxy preferably of 1 to 10 carbon atoms in the aralkoxy backbone (e.g. benzyloxy), phenylthio, and alkylamino preferably of 1 to 8 carbon atoms (e.g. acetamino). Alternatively, $R^3$ and $R^4$, taken together, represent the carbon atoms necessary to complete a fused carbocyclic arylene moiety, such as naphthylene, indylene, or anthrylene, including such ring structures substituted with the other groups identified for $R^3$ and $R^4$.

Stabilizing anions for these diazonium salts are known. These anions make possible the isolation of the salts in dry form and provide for long term thermal stability as well as reduced shock sensitivity.

In the formula above, $X^-$ is preferably the anion of a Lewis acid coordinatively saturated by a hydrogen halide. Useful stabilizing anions include tetrafluoroborate, hexafluorophosphate, chlorozincate and hexafluorotitanate. Of the preferred anions, hexafluorophosphate has been found to be particularly preferred. Other useful anions include arylsulfonates, such as naphthylene disulfonate and 4,4'-biphenyldisulfonate.

In a particularly preferred embodiment, Y is $-SO_2-$, $R^1$ is hydrogen and $R^2$ is carboxymethyl. These compounds form an azobilirubin which has an extremely high extinction coefficient. The currently preferred compound is 4-(N-carboxymethylsulfamyl)-benzene diazonium hexafluorophosphate. Other useful compounds include the following:
  4-[N,N-bis(carboxymethyl)sulfamyl]benzenediazonium hexafluorophosphate;
  4-[N,N-bis(2-hydroxyethyl)sulfamyl]benzenediazonium hexafluorophosphate;

4-(N-carboxymethylcarbamyl)benzenediazonium tetrafluoroborate;

4-(N-carboxypropylcarbamyl)benzenediazonium naphthylenedisulfonate;

4-(N-carboxymethylsulfamyl)benzenediazonium tetrafluoroborate;

4-(N-dodecylsulfamyl)benzenediazonium tetrafluoroborate;

3,5-dichloro-4-(N-carboxymethylsulfamyl)benzenediazonium hexafluorophosphate;

4-(N-carboxymethylsulfamyl)-1-diazonium naphthylene hexafluorophosphate;

7-[N-tris(hydroxymethyl)methylcarbamyl]-4-diazoniumindene hexafluorophosphate; and 4-[N,N-bis(carboxymethyl)sulfamyl]-1-diazonium-6-methoxy naphthylene chlorozincate.

These particularly useful diazonium salts are made by methods which are well known in the art as described, for example, in U.S. Pat. No. 4,468,467 noted hereinabove.

The interactive compositions useful in the determination of total bilirubin preferably include an acid. Where the composition is in the form of an aqueous solution, any acid is useful including mineral acids, such as hydrochloric and sulfuric acids. Where a dry reagent composition is desired, it is preferred to use acids which are solid when anhydrous. Useful acids of this type include malic, sulfosalicylic, tartaric, succinic, phthalic, cyclohexanesulfamic, p-toluenesulfonic and citric. Other useful acids, preformed or formed in situ during the assay, are known to one skilled in clinical chemistry.

The amount of acid used varies widely. Generally, the amount of acid is sufficient to maintain the pH of the reagent composition between about 1 and about 7 when contacted with water. In a preferred embodiment, the acid used is 3,3-dimethylglutaric acid (or equivalent alkali metal salt) which is present in an amount effective to maintain the pH at about 3.5 or less when contacted with water. Reagent compositions and elements utilizing this preferred acid are described in U.S. Ser. No. 597,881 filed on even date herewith by T. W. Wu now U.S. Pat. No. 4,548,905.

The described bilirubin-determining interactive composition also preferably includes what is known in the art as a "diazo bilirubin promoter" (sometimes also referred to as an "accelerating agent"). Useful promoters include dyphylline, caffeine, sodium acetate, sodium benzoate and gum arabic. Dyphylline is a preferred promoter.

The present invention can be practiced with any chemical analyzer constructed to perform rate or endpoint colorimetric assays. Such analyzers can also have the capability of performing potentiometric assays. Such chemical analyzers are illustrated herein in reference to a preferred embodiment illustrated in FIG. 1 which is adapted to perform analytical determinations with dry analytical elements. In FIG. 1 is shown analyzer 12 which comprises a slide supply 12 which is adapted to receive a dry analytical element of the colorimetric type as described herein, and a slide supply 16 which is adapted to receive potentiometric ion-selective electrodes. Each sample of aqueous fluid to be tested is supplied to analyzer 12 in a cup 19 which is supported on analyzer 12 in a tray 20. A metering device 18 is adapted to aspirate sample fluid from a selected cup 19 into a disposable tip 17 selected from tray 20, and then to meter the fluid onto a dry element or electrode in slide distributor 30. A second metering device (not shown) works in conjunction with metering device 18 to deposit reference fluid on potentiometric electrodes.

After the metering operation, potentiometric electrodes are delivered by distributor 30 to an incubator 22, and dry analytical elements of the colorimetric type are delivered to incubator 24. Incubators 22 and 24 are adapted to cooperate, respectively, with response measuring means 23 and 25 which measure the spectrophotometric or potentiometric response in the analytical elements and potentiometric electrodes, respectively. Generally, such a spectrophotometric response is a spectral absorption which can be quantified by measuring the transmission or reflection density in the element with a suitable spectrophotometer containing a light source, photodetector and one or more filters. Such filters, not shown, are placed, if desired, either between the light source and the dry element or between the dry element and the photodetector. This analyzer can also be used to perform rate analyses in which case the dry analytical elements are delivered by distributor 30 to incubator 26 where a series of readings are taken on each element.

Figure 2:
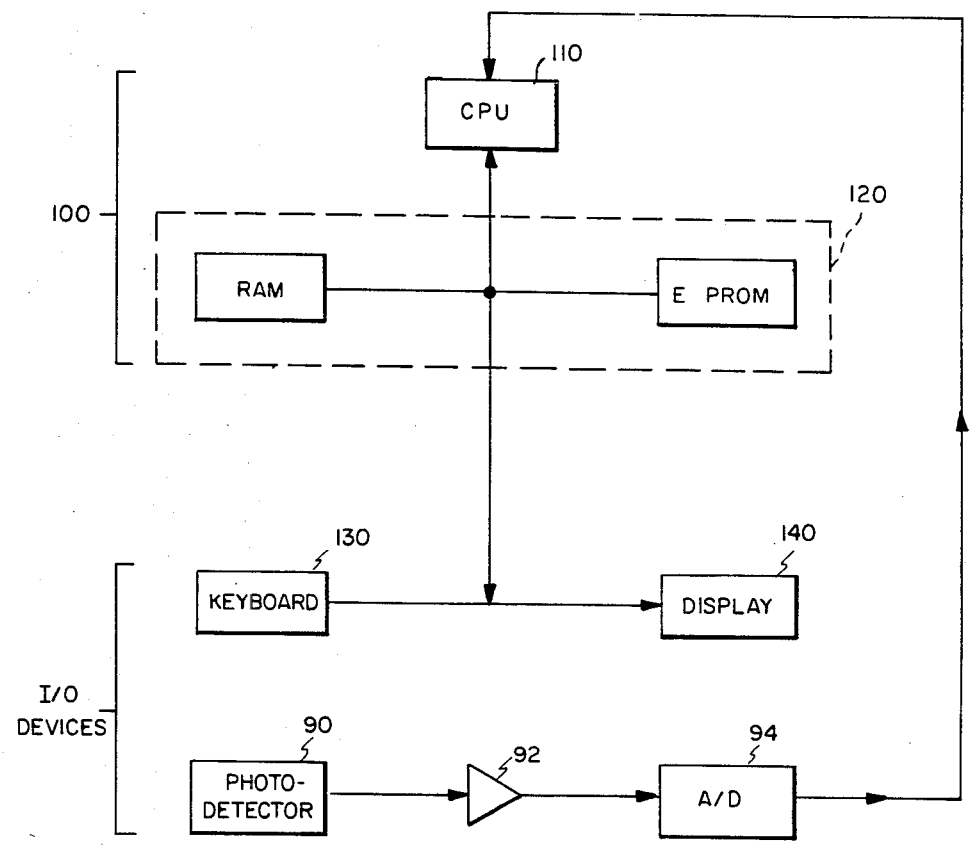
FIG. 2 is a schematic illustration of computing means for the chemical analyzer and its interaction with the photodetector of the analyzer.

Referring to FIG. 2, the signal generated by the photodetector 90 is directed, via amplifier 92 and A/D converter 94, to a computing means 100 which functions with a central processing unit 110 to control the operations and calculations of the analyzer. As is conventional, such computing means can be directly attached to the analyzer or be an off-line component, and includes memory units 120 as known in the art. It can further include input/output (I/O) devices, such as a keyboard 130 and a display 140. Computing means 100 also includes driver interface boards (not shown) to convert computer signals to signals that control the motors of the various moving components of the analyzer.

A variety of conventional computing means (e.g. computer or programmable microprocessor) are useful in supplying the above-noted features. Such computing means of the analyzer calculates the analyte concentration or activity in the test sample using the equation (I):

$$C = a_0 + a_1[A_1 + a_1A_2 + \ldots + a_{n-1}A_n]$$

wherein C is analyte concentration or activity, $A_1, A_2, \ldots A_n$ are the spectrophotometric responses measured at $\lambda_1, \lambda_2, \ldots \lambda_n$, respectively, and $a_0, a_1$ and $a_1, a_2, \ldots a_{n-1}$ are constants determined by the calibration method of this invention described hereinbelow. The wavelengths $\lambda_1, \lambda_2, \ldots \lambda_n$ are determined as described hereinafter. The concentration of an analyte can be determined with an endpoint assay, and the activity of an analyte (e.g. an enzyme) can be determined from a rate assay.

The analyzer can be of any type which has the capability of determining analytes such as by colorimetric, radiometric, fluorometric or potentiometric means and of the type which is capable of doing either endpoint or rate assays. Chemical analyzers which can be adapted for use with the present invention include those described in U.S. Pat. Nos. 4,152,390 (issued May 1, 1979 to Nosco et al); 4,224,032 (issued Sept. 23, 1980 to Glover et al); 4,287,155 (issued Sept. 1, 1981 to Tersteeg et al); and 4,420,566 (issued Dec. 13, 1983 to Jessop et al). Particularly useful chemical analyzers include the EKTACHEM# 400 and 700 analyzers available from Eastman Kodak Company (Rochester, N.Y.).

A chemical analyzer is adapted, or calibrated, to determine an analyte in an aqueous liquid as described herein by the following procedure. Basically, the analyzer must be calibrated by recording therein in some manner the $a_0, a_1$, and $\alpha_1, \alpha_2, \ldots \alpha_{n-1}$ constants which are used in standard equation (I) in analyte determination:

$$C = a_0 + a_1[A_1 + \alpha_1 A_2 + \ldots + \alpha_{n-1} A_n].$$

In determining these constants, a calibrator curve is prepared using samples of known analyte concentration and a suitable reference analytical method. For instance in the illustrated example below for total bilirubin, a calibrator curve is prepared using a modified Jendrassik-Grof reference method [see e.g. Doumas et al, Clin. Chem., 19, pp. 984-993 (1973)] at a wavelength of 600 nm.

A multiplicity (e.g. about 100) of patient test samples (i.e. samples obtained from a random population of patients) are assayed for analyte concentration or activity using the reference method. The number of patient test samples is empirically chosen and can vary widely depending upon the number of samples needed to clearly show the effect of an undefined interferent. Concentrations are determined from the calibration curve. These same patient test samples are than assayed using a conventional assay (e.g. the assay of U.S. Pat. No. 4,468,467, noted hereinabove for total bilirubin determination). Test results which show a significant bias (positive or negative) relative to the reference method on a methods comparison plot indicate test samples which exhibit effects of the undefined interferent during the assay. As used herein, the term "significant" refers to a % bias of greater than about 50%. Bias is a term used to describe the difference between a test value observed with a reference method and the test value observed with the conventional assay. Any of a number of conventional methods are known in the art for a given analyte.

From the multiplicity of patient test samples assayed and plotted as described above, a first patient test sample (thereinafter "biased" sample) is identified which exhibits the significant bias, and a second patient test sample (hereinafter "unbiased" sample) is identified which does not exhibit the significant bias. A spectral absorption scan is then made of each of these patient test samples over the entire range of the visible spectrum. The procedure and equipment used for making such scans are well known in the art.

Absorption bands are then determined from these spectral absorption scans, by plotting a spectral absorption difference scan. Such a scan is a plot of the difference of the two spectral absorption scans obtained by subtracting the scan of the second patient test sample from the scan of the first patent test sample. The absorption difference spectrum characterizes the difference in spectral response between the "biased" test sample and the "unbiased" test sample. Absorption difference spectra and the procedure and equipment used to prepare them are known in the art.

The absorption difference spectrum so prepared will have two or more absorption bands or regions of peak difference up to n absorption bands, including that around primary wavelength $\lambda_1$. Generally, the primary wavelength $\lambda_1$ is chosen as the conventional wavelength at which a given analyte is spectrophotometrically measured. In each absorption band other than the absorption band around $\lambda_1$ is a wavelength which is representative of that band and can be used to correct the test result for interferent effects. At least one of those secondary wavelengths, $\lambda_2, \lambda_3, \ldots \lambda_n$ is chosen for use in the succeeding steps. In the bilirubin example hereinbelow, a single secondary wavelength, $\lambda_2 = 460$, nm was chosen within the absorption band seen in the difference spectrum other than the absorption band at $\lambda_1 = 540$ nm.

Next, using a multiplicity (e.g. at least 100) of patient test samples of known analyte concentrations or activities, a regression line is determined and its intercept and slopes are calculated using standard multiple linear regression analysis and the standard equation (II):

$$C = a_0 + a_1 A_1 + a_2 A_2 + \ldots + a_n A_n$$

wherein C is the known analyte concentration or activity, $A_1, A_2, \ldots A_n$ are the spectrophotometric responses measured with those test samples at $\lambda_1, \lambda_2, \ldots \lambda_n$, respectively; and $a_0$ is the intercept and $a_1, a_2, \ldots a_n$ are the slopes to be determined. For total bilirubin ($B_T$), equation II becomes IIa:

$$B_T = a_0 + a_1 A_1 + a_2 A_2$$

wherein $A_1$ and $A_2$ are the spectrophotometric responses measured at $\lambda_1$ and $\lambda_2$, respectively.

The spectrophotometric responses $A_1, A_2, \ldots A_n$ are either spectral absorbance (in the case of solution assays) or reflection density ($D_R$). Where $D_R$ is not linear with analyte concentration or activity, it is converted to transformed transmission density ($D_T$) where $D_T$ is linear with analyte concentration or activity. The analyzer can be programmed to convert $D_R$ to $D_T$ using what are known in the art as transformation equations. Particularly useful transformation equations are known as Clapper-Williams Transforms which are described by Williams et al in J. Opt. Soc. Am., 43, 595(1953).

Once the constants $a_0, a_1, a_2, \ldots a_n$ are known from the linear regression analysis, the constants $\alpha_1, \alpha_2, \ldots \alpha_{n-1}$ used in equation (I) noted above can be computed using the standard equation (III):

$$\alpha_i = (a_{i+1})/a_1$$

wherein
i = 1 to (n−1).

The constants $a_0, a_1$ and $\alpha_1, \alpha_2, \ldots \alpha_{n-1}$ so determined are then recorded or stored in the analyzer for use during analyte determination when equation (I) is solved for unknown analyte concentration or activity C. These constants can be stored, for example, in computing means 100 (FIG. 2), or on a "soft-copy" of the program which is separately inserted into the analyzer during use. The analyzer can be calibrated as often as desired, for example, as part of routine weekly analyzer calibration procedures or when new lots of reagents, test solutions or analytical elements are used.

Figure 3A:
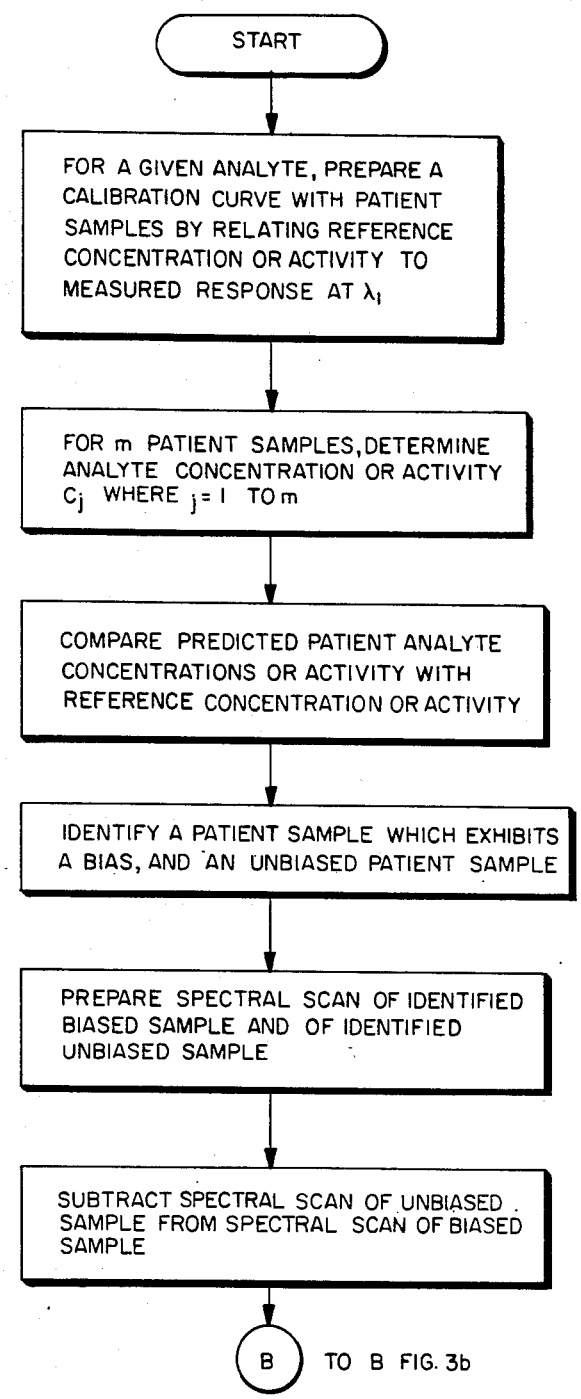
FIGS. 3(a) and 3(b) are a logic flow chart for the programming of the analyzer computing means.
Figure 3B:
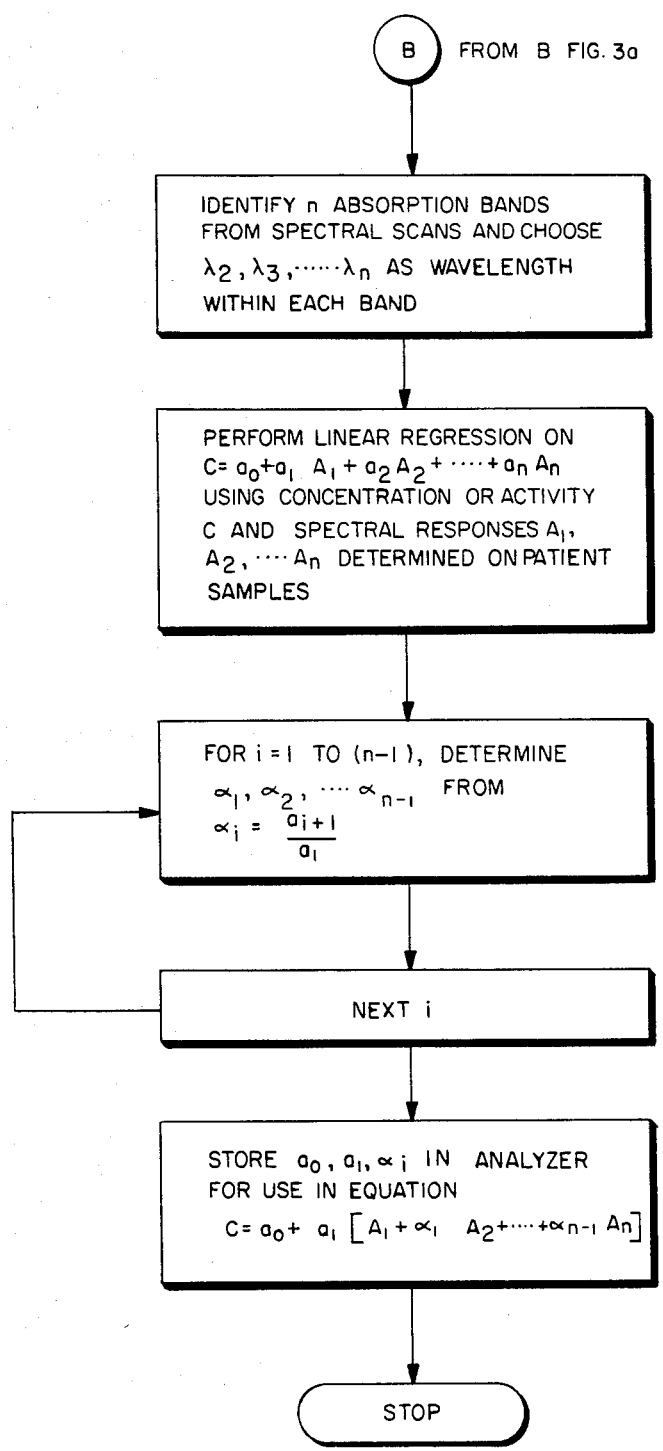

FIGS. 3(a) and 3(b) represents a logic flow chart that is useful in programming a microprocessor to accomplish the above-described calibration method. From this flow chart, a program routine is readily determinable using conventional programming techniques.

The analyte determination method of this invention is adaptable to both solution (i.e. "wet chemistry") and dry element (i.e. "dry chemistry") assays. In solution assays, the assay is carried out entirely in a liquid medium by mixing an aqueous sample to be assayed with a solution containing the interactive composition. The resulting mixture is incubated at an appropriate temperature if desired. This solution assay technique is well known in the art.

When the method is employed with "dry chemistry" elements, the interactive composition can be incorporated into a suitable carrier matrix by imbibition, impregnation, coating or another suitable technique. Useful carrier matrices are insoluble and maintain their structural integrity when exposed to water or physiological fluids such as urine or serum. Useful carrier matrices can be prepared from porous materials such as paper, cellulose, porous particulate structures, wood, glass fiber, woven and nonwoven fabrics (synthetic and nonsynthetic) and the like. A useful dry analytical element is made by imbibing a solution of the reagent composition into the matrix and drying. Useful materials and procedures for making such elements are well known in the art as exemplified in U.S. Pat. Nos. 3,092,465 (issued June 4, 1963 to Adams et al); 3,802,842 (issued Apr. 9, 1974 to Lange et al); 3,915,647 (issued Oct. 28, 1975 to Wright); 3,917,453 (issued Nov. 4, 1975 to Milligan et al); 3,936,357 (issued Feb. 3, 1976 to Milligan et al); 4,248,829 (issued Feb. 3, 1981 to Kitajima et al); 4,255,384 (issued Mar. 10, 1981 to Kitajima et al); and 4,270,920 (issued June 2, 1981 to Kondo et al); U.K. Pat. No. 2,052,057 (published Jan. 21, 1981); and U.S. Pat. Nos. 4,468,467 and 4,548,905, noted hereinabove, as well as the patents noted hereinbelow.

In dry element bilirubin assays, the diazonium salt is generally present at a coverage of at least about 0.05 g/m$^2$, and preferably at a coverage of from about 0.2 to about 2 g/m$^2$.

Preferably, the analytical elements useful in the assay of this invention have at least one porous spreading zone (e.g. which can also be a spreading/reagent zone containing the interactive composition). This zone can be a self-supporting carrier matrix (i.e. composed of a material rigid enough to maintain its integrity), but preferably it is carried on a separate support. Such a support is a substrate made of any suitable dimensionally stable, and preferably, transparent (i.e. radiation transmissive) material which transmits electromagnetic radiation of a wavelength between about 200 and 900 nm. Useful support materials include polystyrene, polyesters [e.g. poly(ethylene terephthalate)], polycarbonates, cellulose esters, etc. The element can have a plurality of zones (spreading, spreading/reagent, reagent, subbing, hydrophilic, mordant, buffer, etc.), some or all containing reagents. These zones are in fluid contact with each other, meaning that fluids can pass between superposed regions of adjacent zones. Stated in another manner, fluid contact refers to the ability to transport components of a fluid between the zones in fluid contact. Preferably, the zones are separate coated layers, although one or more zones can be in a single layer, or one or more separate layers can be in a single zone of an element. Dry element formats and materials are known in the art and described, for example, in U.S. Pat. Nos. 3,992,158 (issued Nov. 16, 1976 to Przybylowicz et al); 4,042,335 (issued Aug. 16, 1977 to Clément); 4,144,306 (issued Mar. 13, 1979 to Figueras); 4,132,528 (issued Jan. 2, 1979 to Eikenberry et al); and 4,258,001 (issued Mar. 24, 1981 to Pierce et al), the disclosures of which are incorporated herein by reference in their entirety.

The porous spreading zone is generally a layer which can accept (i.e. absorb completely) an aqueous liquid sample of at least about 1 $\mu$L. When the sample is applied directly to the zone or provided to it from a zone or zones in fluid contact with it, the sample is distributed such that a uniform concentration of the sample is provided at the surface of the spreading zone facing an adjacent zone. Useful materials for preparing spreading zones are described, for example, in U.S. Pat. Nos. 3,992,158 and 4,258,001, noted hereinabove; and 4,292,272 (issued Sept. 29, 1981 to Kitajima et al); West German OLS No. 3,150,102 (published July 29, 1982); and Japanese Patent Publication 57(1982)-101760 (published June 24, 1982). The spreading zone, for example, can be composed of either fibrous or non-fibrous materials, or both. Preferably, the spreading zone is a nonfibrous, isotropically porous blush polymer spreading layer as described in U.S. Pat. No. 3,992,158, noted hereinabove.

In certain embodiments, dry analytical elements useful for determining total bilirubin in the present invention also include a hydrophilic zone between the support and the spreading zone. This zone can contain a buffer, e.g. 3,3-dimethylglutaric acid, if desired and therefore serve as a buffer zone, as well as any of a variety of hydrophilic binders.

Preferred total bilirubin elements also contain a mordant for azobilirubin in either or both of the above-described hydrophilic or buffer zones. Alternatively, the mordant can be in a separate mordant zone. Such mordants are cationic in nature. Particularly useful mordants are described in U.S. Pat. Nos. 4,069,017 (issued Jan. 17, 1978 to Wu et al) and 4,204,839 (issued May 27, 1980 to Wu et al), the disclosures of which are incorporated herein by reference. A preferred mordant is poly(styrene-co-N-vinylbenzyl-N-benzyl-N,N-dimethylammonium chloride-co-divinylbenzene).

A variety of different elements can be prepared and used in accordance with the present invention. Elements can be configured in a variety of forms, including elongated tapes of any desired width, sheets or chips.

The analyte determination method of this invention can be manual or automated. For example, the amount of analyte (e.g. total bilirubin) in an aqueous liquid is determined by taking an element from a supply roll, slide packet or other source and physically contacting it with a sample of the liquid, e.g. in the chemical analyzer described therein. Such contact can be accomplished in any suitable manner, e.g. dipping or immersing the element into the sample or, preferably, by spotting the element by hand or machine with a drop (e.g. about 2–20 $\mu$L) of the sample by pipette or another suitable dispensing means.

After sample application, the element is exposed to any conditioning, such as incubation, heating or the like, that may be desirable to quicken or otherwise facilitate obtaining any test result.

The analyte (e.g. bilirubin), if present, then reacts with the interactive composition and produces a detectable response or signal, which response is quantifiable by passing the element through a zone in which suitable apparatus (e.g. the chemical analyzer described hereinabove) for spectrophotometric detection (e.g. reflection or transmissive spectrophotometry) is provided.

The spectrophotometric responses are determined at a multiplicity (i.e. two or more) of absorption wavelengths as described hereinabove with regard to the calibration method of this invention. The exact wavelengths chosen to measure absorption are determined by that method and depend upon the analyte and choice of reagents. For example, depending upon the diazonium reagents used for bilirubin determination, the primary wavelength ($\lambda_1$) is within the range of from about 500 to about 580 nm, and preferably at about 540 nm using the preferred diazonium salts noted hereinabove. A secondary wavelength ($\lambda_2$) for total bilirubin is within the range of from about 420 to about 490 nm, and preferably at about 460 nm using the same preferred salts.

The concentration or activity of the analyte, e.g. total bilirubin, is then determined according to equation (I) noted hereinabove.

The following examples are presented to illustrate the practice of this invention. In these examples, the sources of materials were as follows: polyurethane resin as Estane TM 5715 from B. F. Goodrich Co. (Cleveland, Ohio); dyphylline from Aldrich Chemicals Co. (Milwaukee, Wis.); Triton TM X-100 surfactant from Rohm & Haas (Philadelphia, Pa.); Surfactant 10G TM surfactant from Olin Mathieson Corp. (Stamford, Conn.); and the remainder from Eastman Organic Chemicals (Rochester, N.Y.).

EXAMPLE 1

Total Bilirubin Assay Using Dry Analytical Element

This example illustrates the present invention as practiced in determining total bilirubin in human sera.

A dry analytical element having the format and components shown below was prepared and used to determine total bilirubin at $\lambda_1 = 540$ nm according to the teaching of U.S. Pat. No. 4,468,467 noted hereinabove, in a population of human serum samples. In approximately 10% of the serum samples, the predicted total bilirubin values were positively biased from 100–300% as compared to predicted values determined by the modified Jendrassik-Gróf reference method noted hereinabove. It was noted that a majority of the samples giving biased predictions were from hemodialysis or other renal-defective patients. Attempts to isolate the interferent were unsuccessful. Hence, it is believed that the interferent is formed in situ, i.e. when the sample is contacted with the diazonium salt during the assay.

Element Format:

| Spreading/<br>Reagent<br>Layer | Barium sulfate | 50–150 g/m$^2$ |
|---|---|---|
| | Cellulose acetate | 4–12 g/m$^2$ |
| | Polyurethane resin | 0.5–5 g/m$^2$ |
| | Dyphylline | 1–10 g/m$^2$ |
| | Triton X-100 TM surfactant | 0.5–5 g/m$^2$ |
| | 4-(N—carboxymethylsulf-<br>amyl)benzenediazonium<br>hexafluorophosphate | 0.2–2 g/m$^2$ |
| Subbing<br>Layer | Poly(N—isopropylacryl-<br>amide) | 0.1–3 g/m$^2$ |
| Hydrophilic/<br>Layer | Gelatin | 2–12 g/m$^2$ |
| | Gelatin hardener | 0.02–0.2 g/m$^2$ |
| | Malic acid (pH 5) | 1–4 g/m$^2$ |
| | Poly(styrene-co-N—vinyl-<br>benzyl-N—benzyl-N,N—<br>dimethylammonium-<br>chloride-co-divinyl-<br>benzene) | 0.2–2.5 g/m$^2$ |
| | Surfactant 10G TM<br>surfactant | 0.05–1 g/m$^2$ |
| | Poly(ethylene terephthalate)<br>Support | |

The same dry element was used in the practice of this invention and it was found that the positive bias observed with the known assay was substantially eliminated with the present invention.

The improved assay of this invention was accomplished with an EKTACHEM TM 400 clinical chemistry analyzer which had been calibrated to determine total bilirubin ($B_T$) concentration according to the equation (IV):

$$B_T = a_0 + a_1[A_1 + \alpha_1 A_2]$$

which is equation (I) shown hereinabove wherein n is 2. The calibration method of this invention was used to determine the constants $a_0$, $a_1$ and $\alpha_1$ and to record them in the microprocessor of the analyzer.

In particular, the calibration method of this invention was carried out by taking 1615 random population human serum samples and identifying in those samples a first sample which exhibited a significant positive bias with respect to a bilirubin calibration curve generated using the reference method noted above, and second sample not having a bias, but both samples having essentially identical total bilirubin concentration of about 1.5 mg/dL as determined by the reference method. The total bilirubin concentration was evaluated at a primary wavelength $\lambda_1 = 540$ nm which is the conventional absorption wavelength for bilirubin determinations using the assay of U.S. Pat. No. 4,468,467 noted hereinabove. This assay was the conventional assay used in this example.

Spectral scans were plotted for the two identified samples. From a spectral absorption difference scan determined by subtracting the spectral scan of the second sample from the spectral scan of the first sample, it was observed that those scans were quite different over an absorption band centering at about 460 nm. It was thus decided to select 460 nm as a secondary wavelength ($\lambda_2$) for measuring $A_2$ in the above equation (IV) in order to correct for the observed effect of the interferent in the first sample.

Using another random population of about 1100 human serum samples of known bilirubin concentration, a linear regression analysis was performed on equation (IIa)

$$B_T = a_0 + a_1 A_1 + a_2 A_2,$$

wherein $A_1$ and $A_2$ are the transformed transmission densities ($D_T$) observed at $\lambda_1 = 540$ nm and $\lambda_2 = 460$ nm, respectively. The reflection densities ($D_R$) were converted to transformed transmission densities ($D_T$) using the Clapper-Williams Transforms described hereinabove. The constants $a_0$, $a_1$ and $a_2$ were then determined from the regression analysis. The constant $a_0$, which is the intercept of the linear regression line was determined to be $-1.5$; $a_1$ which is the slope of the line with respect to $A_1$ was determined to be 162.5; and $a_2$ which is the slope of the line with respect to $A_2$ was determined to be $-24.25$. Equation IIa was then modified to be (IIb):

$$B_T = -1.5 + 162.5 A_1 - 24.25 A_2.$$

Dividing the last two terms by $a_1$ (i.e. 162.5) gives equation (IIc):

$$B_T = 1.5 + 162.5[A_1 - 0.15 A_2]$$

wherein $\alpha_1 = -0.15$. The values of these constants were than programmed into the EKTACHEM ™ 400 analyzer for use in total bilirubin assays.

These assays were performed by feeding dry analytical elements having the format noted above into the calibrated EKTACHEM ™ 400 analyzer and contacting the elements with a 10 μL sample of each of the 1100 human serum samples noted above. The analyzer calculated the total bilirubin concentrations (mg/dL) according to equation (IIc) by measuring $D_R$ and transforming it into $D_T$. The same serum samples were also evaluated for total bilirubin using the assay of U.S. Pat. No. 4,468,467, noted hereinabove, using an EKTACHEM ™ 400 chemical analyzer which had not been calibrated according to this invention.

Table I presented below lists the data found in this comparison of the two assays. These data are determined from a methods comparison plot which plots the total bilirubin concentration of the method of this invention against the total bilirubin concentration of the conventional method. It is apparent from the data that the assay of this invention reduces the bias observed with the known assay and significantly improves the accuracy of total bilirubin determination. In particular, the Sy·x value for Example 1 was significantly lower than the corresponding Control value. The Sy·x value is a conventional statistic which is a measure of the scatter of data points about the regression line. The lower this value is, the more precise the assay. The r value is a conventional statistic describing the degree of association between the two methods. The closer this value is to 1.0, the more accurate is the assay. The present invention had a r value significantly closer to 1.0 than did the Control assay.

TABLE I

|  | Control | Example 1 |
|---|---|---|
| Sy · x | 0.498 | 0.309 |
| Correlation coefficient(r) | 0.949 | 0.981 |

EXAMPLE 2

Hemoglobin Assay

This example illustrates how the present invention could be practiced to accurately determine hemoglobin in whole blood.

In the conventional Drabkin reaction for determining hemoglobin, whole blood is diluted about 270 times and mixed with an interactive composition for hemoglobin comprising potassium ferricyanide and potassium cyanide to obtain a stable species detectable at 540 nm. It is known that lipemia can cause a significant positive bias in such results (see Caraway, *Amer. J. Clin. Pathol.*, 37, p. 445, 1962).

The present invention can be used to correct for the significant errors that arise in hemoglobin determinations in lipemic specimen samples. The calibration method of this invention would be carried out to determine the $a_0$, $a_1$ and $\alpha_1$, $\alpha_2$, ... $\alpha_{n-1}$ used in equation (I) and store the values in the analyzer. A suitable primary wavelength would be 540 nm. The secondary wavelengths would be ascertained during the calibration procedure. Using these predetermined constants and observed spectrophotometric responses, nonbiased hemoglobin determinations can be made using a conventional interactive composition for hemoglobin.

The invention has been described in detail with particular reference to preferred embodiments thereof, but it will be understood that variations and modifications can be effected within the spirit and scope of the invention.

We claim:

1. A method for calibrating a chemical analyzer useful in the determination of an analyte in an aqueous liquid, said analyzer comprising (a) spectrophotometric means for detecting "n" spectrophotometric responses $A_1$, $A_2$, ... $A_n$ resulting when a sample of said liquid is contacted with an interactive composition for said analyte, and (b) means for calculating the concentration or activity C of said analyte in said sample using the equation (I):

$$C = a_0 + a_1[A_1 + \alpha_1 A_2 + \ldots + \alpha_{n-1} A_n]$$

wherein $a_0$, $a_1$, $\alpha_1$, $\alpha_2$, ... $\alpha_{n-1}$ are defined hereinafter, said method comprising the steps of:

(A) from a multiplicity of patient test samples of unknown analyte concentration or activity, identifying first and second patient test samples having substantially the same analyte concentration or activity, said first sample exhibiting a significant bias in analyte concentration or activity and said second sample exhibiting no significant bias in analyte concentration or activity measured at a primary wavelength $\lambda_1$;

(B) making a spectral absorption scan of each of said samples identified in step A;

(C) identifying absorption bands from said spectral scans where differences in absorbance between said scans can be observed, and selecting at least one secondary wavelength from the group of secondary wavelengths $\lambda_2$, $\lambda_3$, ... $\lambda_n$ representative of said absorption bands of both said first and second patient samples, respectively, wherein n represents the number of absorption bands;

(D) using a multiplicity of patient test samples of known analyte concentration or activity, determining a linear regression line and its intercept and slopes using the equation (II):

$$C = a_0 + a_1 A_1 + a_2 A_2 + \ldots + a_n A_n$$

wherein C is analyte concentration or activity; $a_0$ is the intercept of said line; $A_1$, $A_2$, ... $A_n$ are the spectrophotometric responses measured at $\lambda_1$, $\lambda_2$, ... $\lambda_n$ respectively; and $a_1$, $a_2$, ... $a_n$ are the slopes of said line relating said spectrophotometric responses at $\lambda_1$, $\lambda_2$, ... $\lambda_n$, respectively, to said analyte concentration or activity;

(E) using the results of step D to determine constants $\alpha_1$, $\alpha_2$, ... $\alpha_{n-1}$ for said equation (I) above using the equation (III):

$$\alpha_i = (a_{i+1})/a_1$$

wherein
i = 1 to (n−1); and (F) recording in said analyzer the values of said constants $a_0$, $a_1$, and $\alpha_1$, $\alpha_2$, ... $\alpha_{n-1}$ for use in equation I above.

2. The calibration method of claim 1 wherein said analyte is bilirubin and n is 2.

3. The calibration method of claim 2 wherein $\lambda_1$ is from about 500 to about 580 nm and $\lambda_2$ is from about 420 to about 490 nm.

4. The calibration method of claim 1 wherein said spectrophotometric responses $A_1, A_2, \ldots A_n$ are transformed transmission densities $(D_T)$ determined at $\lambda_1, \lambda_2, \ldots \lambda_n$, respectively.

5. The calibration method of claim 1 wherein said absorption bands are identified in step C by subtracting said spectral scan of said second patient test sample from said spectral scan of said first patient test sample, and making a spectral absorption difference scan.

6. A method for the determination of an analyte in an aqueous liquid, said method comprising the steps of:
(A*) physically contacting a sample of said liquid with an interactive composition for said analyte;
(B*) measuring the spectrophotometric responses $A_1, A_2, \ldots A_n$ resulting from said contact at, respectively, a primary wavelength $\lambda_1$ and at n secondary wavelengths selected from secondary wavelengths $\lambda_2, \lambda_3, \ldots \lambda_n$; and
(C*) determining the concentration or activity C of said analyte using the equation (I):

$$C = a_0 + a_1(A_1 + \alpha_1 A_2 + \ldots + \alpha_{n-1} A_n)$$

wherein the constants $a_0$, $a_1$ and $\alpha_1, \alpha_2, \ldots \alpha_{n-1}$ and said secondary wavelengths $\lambda_2, \lambda_3, \ldots \lambda_n$ are determined according to a calibration method for as many n secondary wavelengths as are used in said step (B*), said calibration method comprising the steps:
(A) from a multiplicity of patient test samples of unknown analyte concentration or activity, identifying first and second patient test samples having substantially the same analyte concentration or activity, said first sample exhibiting a significant bias in analyte concentration or activity and said second sample exhibiting no significant bias in analyte concentration or activity measured at a primary wavelength $\lambda_1$;
(B) making a spectral absorption scan of each of said samples identified in step A;
(C) identifying absorption bands from said spectral scans where differences in absorbance between said scans can be observed, and selecting at least one secondary wavelength from the group of secondary wavelengths $\lambda_2, \lambda_3, \ldots \lambda_n$ representative of said absorption bands of both said first and second patient samples, respectively, wherein n represents the number of absorption bands;
(D) using a multiplicity of patient test samples of known analyte concentration or activity, determining a linear regression line and its intercept and slopes using the equation (II):

$$C = a_0 + a_1 A_1 + a_2 A_2 + \ldots + a_n A_n$$

wherein C is analyte concentration or activity; $a_0$ is the intercept of said line; $A_1, A_2, \ldots A_n$ are the spectrophotometric responses measured at $\lambda_1, \lambda_2, \ldots \lambda_n$ respectively; and $a_1, a_2, \ldots a_n$ are the slopes of said line relating said spectrophotometric responses at $\lambda_1, \lambda_2, \ldots \lambda_n$, respectively, to said analyte concentration or activity;
(E) using the results of step D to determine constants $\alpha_1, \alpha_2, \ldots \alpha_{n-1}$ for said equation (I) above using the equation (III):

$$\alpha_i = (a_{i+1})/a_1$$

wherein
i = 1 to (n−1); and
(F) recording in said analyzer the values of said constants $a_0$, $a_1$, and $\alpha_1, \alpha_2, \ldots \alpha_{n-1}$ for use in equation I above.

7. The method of claim 6 wherein said interactive composition is in a dry analytical element which comprises a support having thereon an isotropically porous spreading zone.

8. The method of claim 7 wherein said element comprises a support having thereon, in order and in fluid contact, a hydrophilic zone and an isotropically porous spreading zone.

9. The method of claim 6 wherein said analyte is bilirubin.

10. The method of claim 9 wherein n is 2 and the concentration of total bilirubin $(B_T)$ in said liquid is determined using the equation:

$$B_T = a_0 + a_1[A_1 + \alpha_1 A_2]$$

wherein $a_0$, $a_1$ and $\alpha_1$ are constants determined according to said calibration method, and $A_1$ and $A_2$ are spectrophotometric responses detected at $\lambda_1$ and $\lambda_2$, respectively.

11. The method of claim 10 wherein $\lambda_1$ is from about 500 to about 580 nm and $\lambda_2$ is from about 420 to about 490 nm.

12. The method of claim 9 wherein said interactive composition comprises a diazonium salt which is represented by the structure:

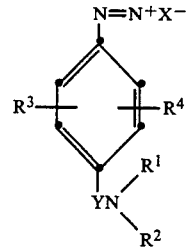

wherein $X^-$ is a stabilizing anion; Y is —CO— or —$SO_2$—; $R^1$ and $R^2$ are independently selected from hydrogen, alkyl, alkaryl, aryl, carboxyalkyl and hydroxyalkyl; and $R^3$ and $R^4$ are independently selected from groups such that the sum of the Hammett sigma values for $R^3$ and $R^4$ does not exceed +0.4 or $R^3$ and $R^4$, taken together, represent the carbon atoms necessary to complete a fused carbocyclic arylene moiety.

13. The method of claim 12 wherein $X^-$ is an anion of a Lewis acid coordinatively saturated by a hydrogen halide, Y is —$SO_2$—, $R^1$ is hydrogen and $R^2$ is carboxymethyl.

14. The method of claim 6 wherein said spectrophotometric responses $A_1, A_2, \ldots A_n$ are transformed transmission densities $(D_T)$ determined at $\lambda_1, \lambda_2, \ldots \lambda_n$, respectively.

15. A chemical analyzer for the determination of an analyte in an aqueous liquid in contact with an interactive composition for said analyte;
said analyzer comprising
means for measuring the spectrophotometric responses $A_1, A_2, \ldots A_n$ at, respectively, a primary wavelength $\lambda_1$ and at n secondary wavelengths selected from the secondary wavelengths $\lambda_2, \lambda_3, \ldots \lambda_n$; and means for determining the concentration or activity C of said analyte using the equation (I):

$$C = a_0 + a_1(A_1 + \alpha_1 A_2 + \ldots + \alpha_{n-1} A_n)$$

wherein the constants $a_0$, $a_1$ and $\alpha_1, \alpha_2, \ldots \alpha_{n-1}$ and said secondary wavelengths $\lambda_2, \lambda_3, \ldots \lambda_n$ are determined according to a calibration method for as many n secondary wavelengths as are used, said calibration method comprising the steps:
- (A) from a multiplicity of patient test samples of unknown analyte concentration or activity, identifying first and second patient test samples having substantially the same analyte concentration or activity, said first sample exhibiting a significant bias in analyte concentration or activity and said second sample exhibiting no significant bias in analyte concentration or activity measured at a primary wavelength $\lambda_1$;
- (B) making a spectral absorption scan of each of said samples identified in step A;
- (C) identifying absorption bands from said spectral scans where differences in absorbance between said scans can be observed, and selecting at least one secondary wavelength from the group of secondary wavelengths $\lambda_2, \lambda_3, \ldots \lambda_n$ representative of said absorption bands of both said first and second patient samples, respectively, wherein n represents the number of absorption bands;
- (D) using a multiplicity of patient test samples of known analyte concentration or activity, determining a linear regression line and its intercept and slopes using the equation (II):

$$C = a_0 + a_1 A_1 + a_2 A_2 + \ldots + a_n A_n$$

wherein C is analyte concentration or activity; $a_0$ is the intercept of said line; $A_1, A_2, \ldots A_n$ are the spectrophotometric responses measured at $\lambda_1, \lambda_2, \ldots \lambda_n$ respectively; and $a_1, a_2, \ldots a_n$ are the slopes of said line relating said spectrophotometric responses at $\lambda_1, \lambda_2, \ldots \lambda_n$, respectively, to said analyte concentration or activity;
- (E) using the results of step D to determine constants $\alpha_1, \alpha_2, \ldots \alpha_{n-1}$ for said equation (I) above using the equation (III):

$$\alpha_i = (a_{i+1})/a_1$$

wherein
i = 1 to (n−1); and
- (F) recording in said analyzer the values of said constants $a_0$, $a_1$, and $\alpha_1, \alpha_2, \ldots \alpha_{n-1}$ for use in equation I above.

16. The analyzer of claim 15 wherein said determining means comprises a computing means.

17. The analyzer of claim 15 wherein said computing means comprises a programmable microprocessor.

18. The analyzer of claim 15 adapted to determine said analyte with a dry analytical element.

* * * * *